(12) United States Patent
Pilly et al.

(10) Patent No.: US 10,720,076 B1
(45) Date of Patent: Jul. 21, 2020

(54) CLOSED-LOOP MODEL-BASED CONTROLLER FOR ACCELERATING MEMORY AND SKILL ACQUISITION

(71) Applicant: HRL Laboratories, LLC, Malibu, CA (US)

(72) Inventors: Praveen K. Pilly, West Hills, CA (US); Michael D. Howard, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 186 days.

(21) Appl. No.: 15/682,065

(22) Filed: Aug. 21, 2017

Related U.S. Application Data

(60) Provisional application No. 62/410,533, filed on Oct. 20, 2016.

(51) Int. Cl.
  *G09B 19/00* (2006.01)
  *A61B 5/00* (2006.01)
  *A61B 5/0476* (2006.01)

(52) U.S. Cl.
  CPC ............ *G09B 19/00* (2013.01); *A61B 5/0476* (2013.01); *A61B 5/4812* (2013.01)

(58) Field of Classification Search
  None
  See application file for complete search history.

(56) References Cited

U.S. PATENT DOCUMENTS

| 5,722,418 A | 3/1998 | Bro |
| 2012/0251989 A1 | 10/2012 | Wetmore et al. |
| 2014/0051045 A1 | 2/2014 | Stiults et al. |

FOREIGN PATENT DOCUMENTS

WO WO 03-067555 8/2003

OTHER PUBLICATIONS

Notification of Transmittal of International Search Report and the Written Opinion of the International Searching Authority for PCT/US2017/047865; dated Nov. 27, 2017.
International Search Report of the International Searching Authority for PCT/US2017/047865; dated Nov. 27, 2017.
Written Opinion of the International Searching Authority for PCT/US2017/047865; dated Nov. 27, 2017.

(Continued)

*Primary Examiner* — James B Hull
(74) *Attorney, Agent, or Firm* — Tope-McKay & Associates

(57) ABSTRACT

Described is a closed-loop control system for memory consolidation in a subject. During operation, the system encodes information regarding environmental items as memories in both a long-term memory store and a short-term memory store. The system generates an activation level representation of a memory of interest related to at least one of the environmental items. An association strength representation for the memories is also generated. Memory consolidation is simulated when the subject is in NREM sleep or quiet waking by strengthening the association strength representation related to the memory of interest. The system predicts behavioral performance for the memory of interest as a probability that the memory of interest can be recalled on cue. When the behavioral performance is below a threshold, an intervention system can be activated.

24 Claims, 8 Drawing Sheets

(56) References Cited

OTHER PUBLICATIONS

Alex Lilijecrantz, "Memory Consolidation in Artificial Neural Networks," 2 003, https://www.nada.kth.se/utbildning/grukth/exjobb/rapportlistor/2003/rapporter03/liljencrantz_axel_03148.pdf, see pp. 6-7.

Rudoy JD, Voss JL, Westerberg CE, Paller KA. Strengthening Individual Memories by Reactivating Them During Sleep. Science. 2009; 326: pp. 1079-1079.

Diekelmann S, Biggel S, Rasch B, Born J. Offline consolidation of memory varies with time in slow wave sleep and can be accelerated by cuing memory reactivations. Neurobiol. Learn. Mem. 2012; 98: pp. 103-111.

Marshall L, Helgadóttir H, Mölle M, Born J. Boosting slow oscillations during sleep potentiates memory. Nature. 2006; 444: pp. 610-613.

Kato Y, Endo H, Kizuka T. Mental fatigue and impaired response processes: event-related brain potentials in a Go/NoGo task. Int. J. Psychophysiol. Off. J. Int. Organ. Psychophysiol. 2009; 72: pp. 204-211.

Henckens MJAG, Hermans EJ, Pu Z, Joëls M, Fernández G. Stressed Memories: How Acute Stress Affects Memory Formation in Humans. J. Neurosci. 2009; 29: pp. 10111-10119.

Akin M, Kurt MB, Sezgin N, Bayram M. Estimating vigilance level by using EEG and EMG signals. Neural Comput. Appl. 2007; 17: pp. 227-236.

Jaar O, Pilon M, Carrier J, Montplaisir J, Zadra A. Analysis of Slow-Wave Activity and Slow-Wave Oscillations Prior to Somnambulism. Sleep. 2010; 33: pp. 1511-1516.

Itti L, Koch C. A saliency-based search mechanism for overt and covert shifts of visual attention. Vision Res. 2000; 40: pp. 1489-1506.

Botteldooren D, DeCoensel B. The role of saliency, attentio n and source identification in soundscape research. ProcInternoise 2009 [Internet]. Ottowa, Canada; 2009, pp. 1-9, Available from http://citeseerx.ist.psu.edu/viewdoc/download?doi=10.1.1.468.8119&rep=rep1&type=pdf.

Lebiere C, Pirolli P, Thomson R, Paik J, Rutledge-Taylor M, Staszewski J, et al. A Functional Model of Sensemaking in a Neurocognitive Architecture. Comput. Intell. Neurosci. [Internet]. vol. 2013, pp. 1-29, Article ID 921695. Available from: http://www.hindawi.com/journals/cin/2013/921695/abs/.

Euston DR, Gruber AJ, McNaughton BL. The role of medial prefrontal cortex in memory and decision making. Neuron. 2012; 76: pp. 1057-1070.

Communication pursuant to Rules 161(2) and 162 EPC for European Regional Phase Patent Application No. 17861769.2, dated May 28, 2019.

Response to the communication pursuant to Rules 161(2) and 162 EPC for European Regional Phase Patent Application No. 17861769.2, dated Dec. 6, 2019.

Correction for Chinese Patent Application No. 201780057906.9, dated Jun. 12, 2019.

International Preliminary Report on Patentability for PCT/US2017/047865; dated Nov. 15, 2018.

Notification of International Preliminary Report on Patentability for PCT/US2017/047865; dated May 2, 2019.

International Preliminary Report on Patentability for PCT/US2017/047865; dated May 2, 2019.

US 10,720,076 B1

CLOSED-LOOP MODEL-BASED CONTROLLER FOR ACCELERATING MEMORY AND SKILL ACQUISITION

GOVERNMENT RIGHTS

This invention was made with government support under a U.S. Government contract, Contract Number W911NF-16-C-0018. The government has certain rights in the invention.

CROSS-REFERENCE TO RELATED APPLICATIONS

This is a non-provisional patent application of 62/410,533, filed on Oct. 20, 2016, the entirety of which is hereby incorporated by reference.

BACKGROUND OF INVENTION

(1) Field of Invention

The present invention relates to memory acquisition system and, more particularly, to a closed-loop model-based control system for the enhancement of devices used for memory consolidation, learning and skill acquisition in human subjects.

(2) Description of Related Art

It is widely reported that new memories are first encoded into short-term memory in the hippocampus, and then gradually over a period of days, weeks, or months, they are consolidated into slower-learning cortex where they are slowly integrated non-destructively into the long-term memory. Once consolidated into long-term memory they become more resistant to decay. This consolidation process is called "replay", and occurs during a deep stage of sleep called non-rapid-eye-movement sleep or NREM. The theory holds that the more often a memory is replayed, the better the subject performs when tested. Although any memory in the hippocampus has a chance of being replayed during sleep, there is a higher probability that a specific memory will be replayed if it was related to some emotional content or high immediate reward. Unfortunately, many things that one may need to learn are boring or tedious, and the reward for learning them may be a long way off.

Further, in operational tasks (as in many business and educational scenarios), it can be critically important to quickly integrate new information (based on limited exposure) and accurately recall it. As noted above, it has been widely accepted that memories are consolidated during sleep, and there have been a few laboratory experiments that have implemented some targeted interventions to improve memory consolidation. For example, in state of the art laboratory experiments, auditory or olfactory cues are associated with toy tasks (such as a "concentration" memory game where users had to remember the location of pairs of images in a matrix) during task performance, and these cues are then used during sleep to trigger replays of that task performance memory. On the next day, memories for which replays had been cued during sleep are consolidated, as evidenced by improved performance upon testing.

By way of example, Rudoy (see the List of Incorporated References, Reference No. 1) described a system directed to recalling object location and sound. Their results demonstrated a 97% recall after 1.5 hours, but only 4% recall after 48 hours. In other art, Diekelman (see Literature Reference No. 2) was directed to object location and odor, and demonstrated an 84% recall after 1.67 hours, but only 5% recall after 10 hours. In yet other art, Marshal (see Literature Reference No. 3) was directed to paired associates and transcranial direct-current stimulation (tDCS). Marshal's work resulted in a 90% recall after 8.5 hours and 88.2% recall after 10 hours.

The abovementioned prior art memory intervention techniques have only been tested in a laboratory, under supervised sleep conditions. None of these were ever intended for real-world use; only for research on memory consolidation. The intervention delivery system must be automated to make any such device into a commercial product that could be used by individuals apart from a supervised laboratory setting.

Notably, none of these prior art references incorporates a model-based intervention system to control the application of the cues during sleep based on a simulation of the behavior improvement based on the treatment given so far. Such a model-based control system could be used to automatically determine whether the intervention should be continued or should be stopped, based on the estimated level of performance. There are several benefits to such a capability: (1) It limits the number of times the subject must be exposed to the intervention. This is most important for interventions that use up limited resources (like electricity from a battery, or aromas from some oil reservoir), or interventions that some may not want to be applied more than necessary (like transcranial stimulation). (2) It stops the intervention once the estimated level of performance has been reached, allowing other memories a chance to be consolidated. If a single memory were to be cued indiscriminately throughout the night, it could crowd out other memories. (3) Once that level of performance has been reached and the intervention has been stopped, if interfering memories are replayed, the desired level of performance may decay. Such a controller could continue estimating performance on the skill or skills and turn back on the intervention if necessary to get it back up to the desired level.

Thus, a continuing need exists for a model-based control system to control a memory consolidation improvement intervention, by simulating the level of behavioral performance throughout the night, based upon an already administered treatment, by assessing the subject's brain state and deciding in real time when the intervention should be applied.

SUMMARY OF INVENTION

Described is a closed-loop control system for memory consolidation in a subject. In various aspects, the system includes one or more processors and a memory, the memory being a non-transitory computer-readable medium having executable instructions encoded thereon, such that upon execution of the instructions, the one or more processors perform several operations. For example, during operation, the system encodes information regarding environmental items as memories in both a long-term memory store and a short-term memory store. An activation level representation of a first memory is generated, the first memory being a memory of interest related to at least one of the environmental items. Further, association strength representations are generated for the memories. The system also simulates memory changes (e.g., consolidation) of the first memory in a subject while the subject is coupled to an intervention system. Memory consolidation is simulated when the subject is in NREM sleep or quiet waking by strengthening the association strength representation related to the memory of interest. Based on the simulated memory changes, the system predicts behavioral performance for the first memory, the behavioral performance being a probability that the first memory can be recalled on cue. Finally, the system controls operation of the intervention system (e.g., turning on and off) with respect to the first memory based on the behavioral performance of the first memory determined by the simulation. For example, when the behavioral performance is below a threshold, an intervention system can be activated.

In another aspect, encoding information regarding environmental items includes encoding descriptive attribute-value pairs and encoding parameters.

Further, information is encoded in both the long-term memory and short-term memory at the same time, at their respective learning rates.

In yet another aspect, an output of the short-term memory is the input of long-term memory, such that when an item is recalled from the short-term memory, its associations are strengthened in the long-term memory.

In yet another aspect, the encoding parameters include both timestamp data and physiological measurements of a subject.

Further, the memory of interest is a sequence of events or a single event.

In another aspect, the activation level representation is a function of physiological measurements taken at time of encoding the memory of interest. Additionally, the activation level representation decays at a higher rate in the short-term memory than in the long-term memory.

In yet another aspect, the system controls operation of the intervention system with respect to a second memory based on the behavioral performance of the second memory determined by the simulation.

Further, predicting behavioral performance of the first memory occurs each time a replay event occurs or at regular intervals through slow wave sleep duration.

In yet another aspect, at least one of time constants and modulation parameters is tuned to cause the predicted behavioral performance match empirical behavioral data of the subject.

In another aspect, the system performs an operation of controlling interventions for one or more memories of interest by activating interventions for memories that are needed to increase memory consolidation and deactivating interactions for memories that correspond to memories that are consolidated according to a corresponding predicted performance that exceeds a threshold.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
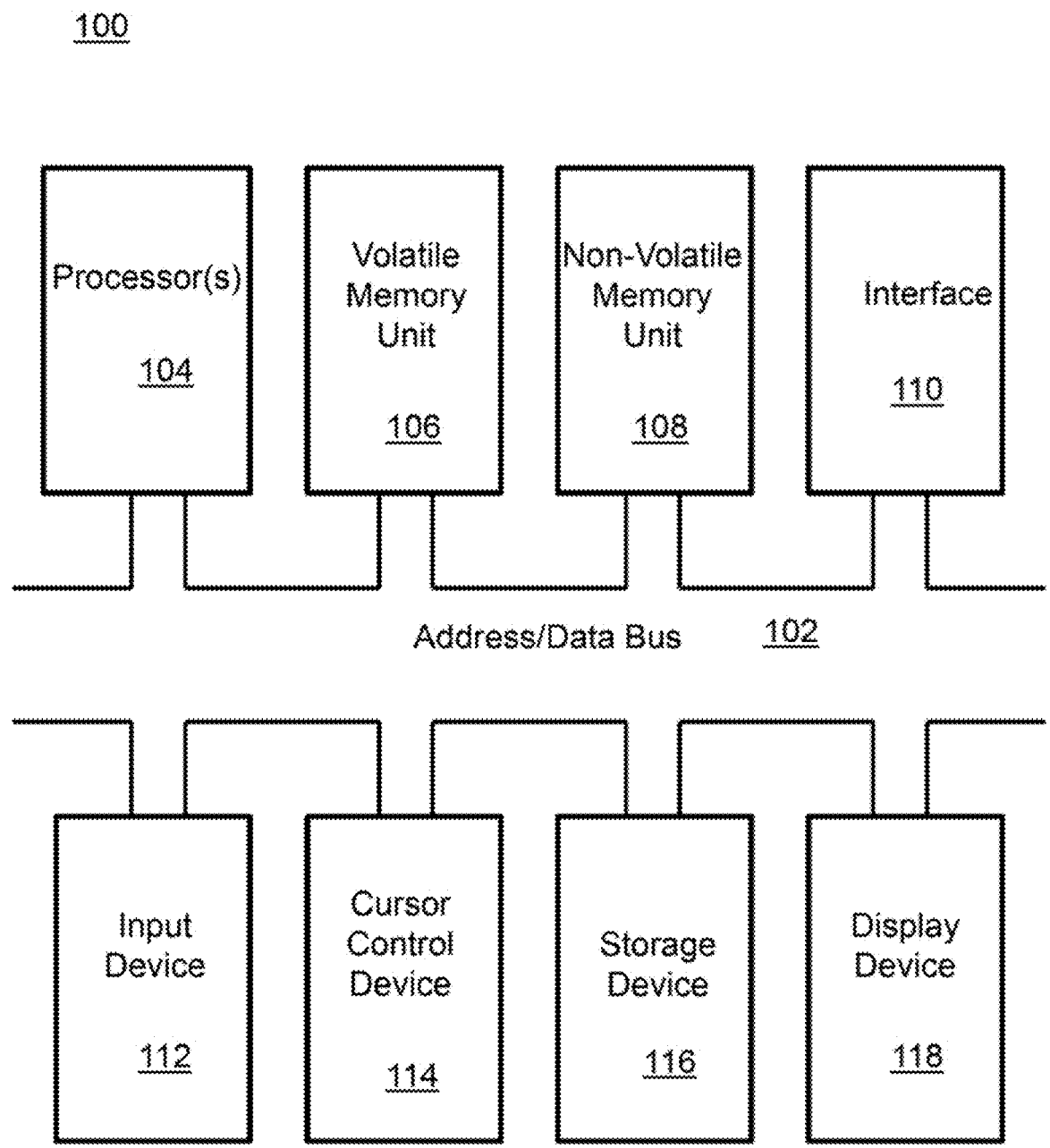
FIG. 1 is a block diagram depicting the components of a system according to various embodiments of the present invention.

The present invention relates to a memory consolidation system and, more particularly, to a closed-loop model-based control system for the enhancement of devices used for memory consolidation, learning and skill acquisition in human subjects. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Rudoy J D, Voss J L, Westerberg C E, Paller K A. Strengthening Individual Memories by Reactivating Them During Sleep. Science. 2009; 326: 1079-1079.
2. Diekelmann S, Biggel S, Rasch B, Born J. Offline consolidation of memory varies with time in slow wave sleep and can be accelerated by cuing memory reactivations. Neurobiol. Learn. Mem. 2012; 98: 103-11.
3. Marshall L, Helgadottir H, Molle M, Born J. Boosting slow oscillations during sleep potentiates memory. Nature. 2006; 444: 610-3.
4. Kato Y, Endo H, Kizuka T. Mental fatigue and impaired response processes: event-related brain potentials in a Go/NoGo task. Int. J. Psychophysiol. Off. J. Int. Organ. Psychophysiol. 2009; 72: 204-11.
5. Henckens MJAG, Hermans E J, Pu Z, Joels M, Fernandez G. Stressed Memories: How Acute Stress Affects Memory Formation in Humans. J. Neurosci. 2009; 29: 10111-9.
6. Akin M, Kurt M B, Sezgin N, Bayram M. Estimating vigilance level by using EEG and EMG signals. Neural Comput. Appl. 2007; 17: 227-36.
7. Jaar O, Pilon M, Carrier J, Montplaisir J, Zadra A. Analysis of Slow-Wave Activity and Slow-Wave Oscillations Prior to Somnambulism. Sleep. 2010; 33: 1511-6.
8. Itti L, Koch C. A saliency-based search mechanism for overt and covert shifts of visual attention. Vision Res. 2000; 40: 1489-506.
9. Botteldooren D, DeCoensel B. The role of saliency, attention and source identification in soundscape research. ProcInternoise 2009 [Internet]. Ottowa, Canada; 2009, Available from http://citeseerx.ist.psu.edu/viewdoc/download?doi=10.1.1.468.8119&rep=rep1&type-pdf.
10. Lebiere C, Pirolli P, Thomson R, Paik J, Rutledge-Taylor M, Staszewski J, et al. A Functional Model of Sensemaking in a Neurocognitive Architecture. Comput. Intell. Neurosci. [Internet]. vol. 2013, Article ID 921695. Available from: http://www.hindawi.com/journals/cin/2013/921695/abs/.
11. Euston D R, Gruber A J, McNaughton B L. The role of medial prefrontal cortex in memory and decision making. Neuron. 2012; 76: 1057-70.

(2) Principal Aspects

Various embodiments of the invention include three "principal" aspects. The first is a system for the enhancement of memory consolidation, learning and skill acquisition in human subjects. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
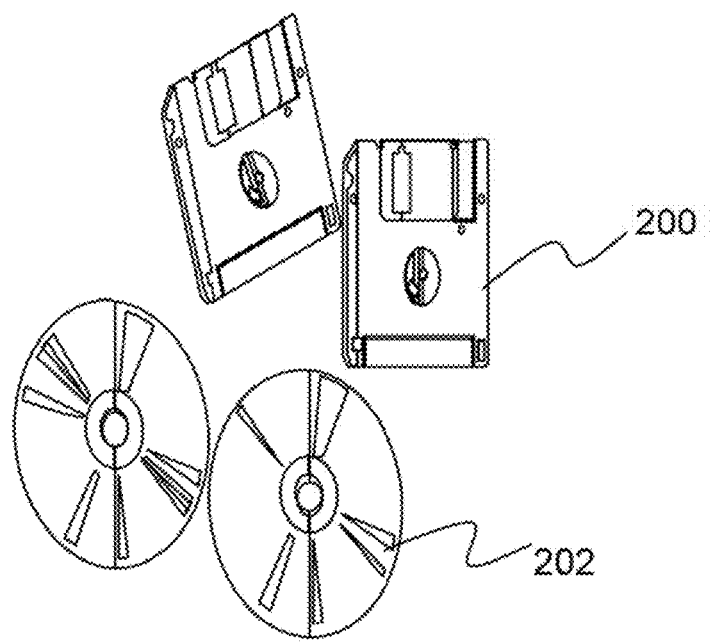
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

This disclosure provides a closed-loop model-based control system that is a useful addition to improve the efficacy and efficiency of interventions used to improve consolidation of specific memories; e.g., memories of specific things that must be learned quickly and remembered clearly and easily. There are several prior art interventions (listed below) that can be improved upon by adding the closed-loop system of this disclosure. The model described herein simulates, at a functional level, the encoding and consolidation of memories, and makes predictions of the resulting behavioral performance (i.e., the subsequent ability to recall and use memories of interest). Used in a control loop with brain sensors and an intervention system (e.g., transcranial current stimulation, odor, or auditory cues, etc.), this model simulated memory acquisition during waking and consolidation during sleep, and during sleep it activates the intervention system until the behavioral predictions reach a desired level, at which time the model deactivates the intervention. Importantly, the model of the present disclosure makes these predictions in real-time (optimally at the speed of slow-wave sleep oscillations in NREM sleep, ~1 Hz; slower operation just limits the number of applications of the intervention during the night), for closed-loop control of the memory consolidation process. Such a control system for a memory improvement intervention, using behavioral performance predictions to decide when interventions are needed during sleep, has never been previously conceived or implemented.

In operational tasks (as in many business and educational scenarios), it can be critically important to quickly integrate new information (based on limited exposure) and accurately recall it. Thus, a purpose of this disclosure is to control interventions that enhance memory consolidation to make this possible. Although it is widely accepted that memories are consolidated during sleep, and there have been a few laboratory experiments that have implemented some targeted interventions, the system of this disclosure is the first to implement a control loop around an intervention. The system implements the control loop to control exactly when an intervention should be applied in order to achieve the desired level of performance.

The system will automatically determine when and if certain interventions should be applied during sleep and quiet waking periods. The system does this by predicting behavioral performance outcomes resulting from memory replay activity in real-time during quiet waking or slow wave sleep, thereby allowing selection of the best replay intervention options to achieve a desired performance. When the predicted performance reaches the desired level, the model turns off the interventions, allowing other memories to be consolidated. The model is shaped by the sequence and content of all experienced stimuli in a situational paradigm, as well as the characteristics of prior replay events, so it can predict the impact that further intervention will have on behavior. Without the control system described herein, the interventions during sleep to improve consolidation of a specific memory or memories are uninformed: there would be no way to test behavioral performance until the subject wakes up. If the interventions are applied more than necessary, it can prevent other memories from being consolidated, which can be harmful. Alternatively, if the interventions are applied less than necessary, the desired behavioral performance will not be achieved.

The present invention will allow, for the first time, a targeted personalized closed-loop system for enhancing memory in both normal subjects and those with learning difficulties related to memory consolidation. As can be appreciated by those skilled in the art, such a system could be used for training (e.g., pilot training), or as a commercial product. Since there is recent widespread interest into brain enhancement technologies, and there are several commercial systems on the market today, the control technique system of the present invention can be easily incorporated into a variety of existing or new memory intervention products. As a non-limiting example, the closed-loop model-based controller of the present invention can be utilized with the transcranial current stimulation memory intervention systems produced by Neurolectrics, Soterix Medical, and/or EGI. Neurolectrics is located at 210 Broadway, Suite 201, Cambridge 02139, Massachusetts, USA. Soterix Medical is located at 237 W 35th St, New York, N.Y. 10001, while EGI (or Electrical Geodesics, Inc.) is located at 500 East 4th Ave., Suite 200, Eugene, Oreg. 97401. The closed-loop memory-based controller could also be used with the audio or odor memory interventions used in university laboratories as mentioned above.

Products that incorporate the present invention will enable people to reinforce episodic memories and acquire skills faster while they sleep. The present invention, when paired with a memory consolidation or intervention technique, automates the supervision required to apply the technique, and makes it unnecessary to apply the intervention indiscriminately throughout the night. Thus, the present invention is part of the transition to move these techniques out of clinical settings and into home use.

(4) Specific Details of Various Embodiments

As noted above, memory intervention techniques or products have been devised in an attempt to improve memory consolidation into long-term memory for replay. The present invention is not another intervention; rather, it is an automation technique~an intervention control system that will improve the effectiveness and efficiency of any of interventions that produce replay of specific memories.

In various embodiments, the model of this disclosure quantitatively simulates the impact of sleep on long-term memory function and teases apart equally important contributions from wake encoding and sleep consolidation. Its subject-specific predictive power in the context of task performance comes from simulating non-invasively assessed markers of attention during encoding as well as duration and quality of consolidation periods. Specific details are provided below.

(4.1) Basic Architectural Diagram

Figure 3:
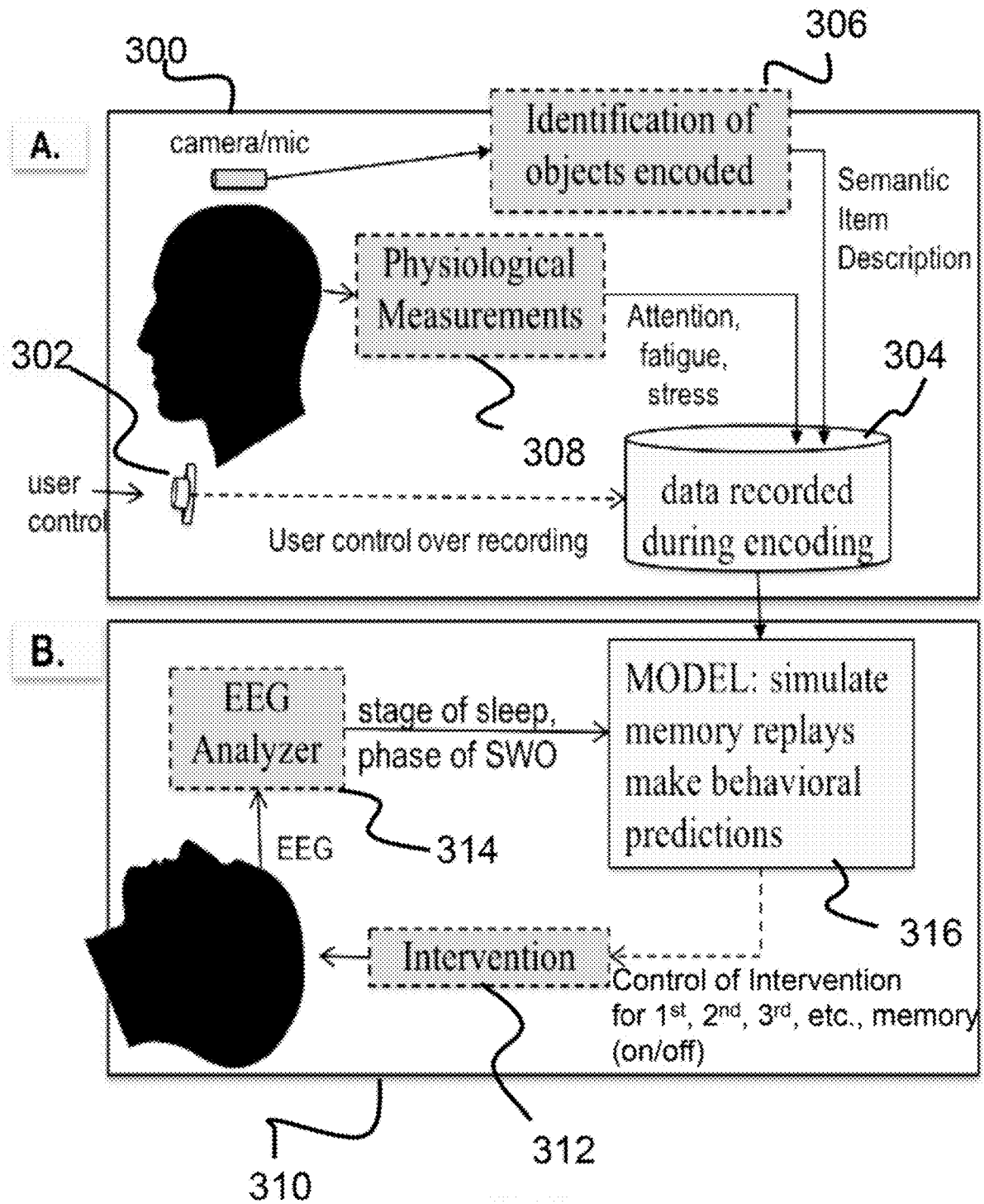
FIG. 3 is a diagram of the closed-loop model-based control system according to various embodiments of the present invention.

FIG. 3 illustrates the basic setup for the closed-loop model based controller according to various embodiments of the present disclosure. Component A captures data during waking 300 for model updating, while component B simulates memory consolidation (changes) of a first memory, etc., during sleep 310 or quiet waking periods. The model simulates behavioral performance and controls when to apply the intervention when the subject is coupled to the intervention system.

During waking experience 300, a user control 302 initiates data recording 304 (into, for example, a database) when an event to be remembered is about to take place. For example, the device would be turned on while instructor is shows the user how to perform a skill like a tennis serve, or while the user practices playing a difficult musical passage slowly and accurately, or while a student studies multiplication tables. The identification of objects (e.g., tennis racket and ball, etc.) encoded 306 can be manually input or automatically input using any suitable object identification system as known to those skilled in the art. The computational model will simulate the gain in short-term memory of the skill during the event, and then simulate the decay of that memory whenever the user is not studying the event. The simulation incorporates physiological measurements to use as a modulator on the learning rate. The reasoning is that if the user is paying attention to the skill and is not fatigued or stressed, the learning rate should be higher than with low attention, fatigue, and stress.

Physiological measurements 308 can be obtained from the user to determine attention, fatigue, or stress. For example, electroencephalogram (EEG), electromyogram (EMG), and/or electrocardiogram (ECG) readings can be taken of the user. Mental fatigue significantly modulates the amplitude of certain event-related potentials (ERPs) (see Literature Reference No. 4), and stress can be inferred from electrocardiogram (ECG) read-out of heart rate variability. A small amount of stress improves encoding strength (see Literature Reference No. 5). Attention, or vigilance, can be estimated from EEG and EMG (see Literature Reference No. 6).

At the end of a day in which a memory of a specific event was trained and/or tested, the system can be employed during a sleep phase 310. The system includes an intervention module 312 employed in the sleep phase 310 that reapplies the odor, a sound, or electrical stimulation cue that was associated with the memory during waking, to a cue recalls of the specific cued memory. The intervention module 312 is any suitable module that applies the aforementioned intervention, non-limiting examples of which include the modules described in Literature Reference Nos. 1 and 2. The system also includes an EEG Analyzer module 314 that can detect the sleep phase 310 or stage, including detection of Slow Wave Oscillations (SWO) that occur mostly during the deepest stages of sleep (non-rem stage 3 and 4), although they can occur during times of deep restfulness in a quiet waking state as well. For online operation, only a rolling window of the data need be kept, just enough to assess the identity of the last replay (e.g., a 400 ms~is temporal window of the positive phase of the last slow wave oscillation). The EEG Analyzer module 314 is any suitable module that is operable to provide the aforementioned operation. For example, sleep stages are detectable by widely available commercial sleep monitors. The phase of SWO can be ascertained currently by analysis of the EEG signal using any suitable technique known to those skilled to the art, a non-limiting example of which includes the technique described in Literature Reference No. 7. The close-loop controller, then, is the control system that turns the intervention on or off based on a prediction of the intervention's effect on the behavioral result. Such predictions are provided by a memory replay model 316, which simulates the replay of memories during sleep, and predicts the behavioral results of such replay.

(4.2) Memory Replay Computational Model

Figure 4:
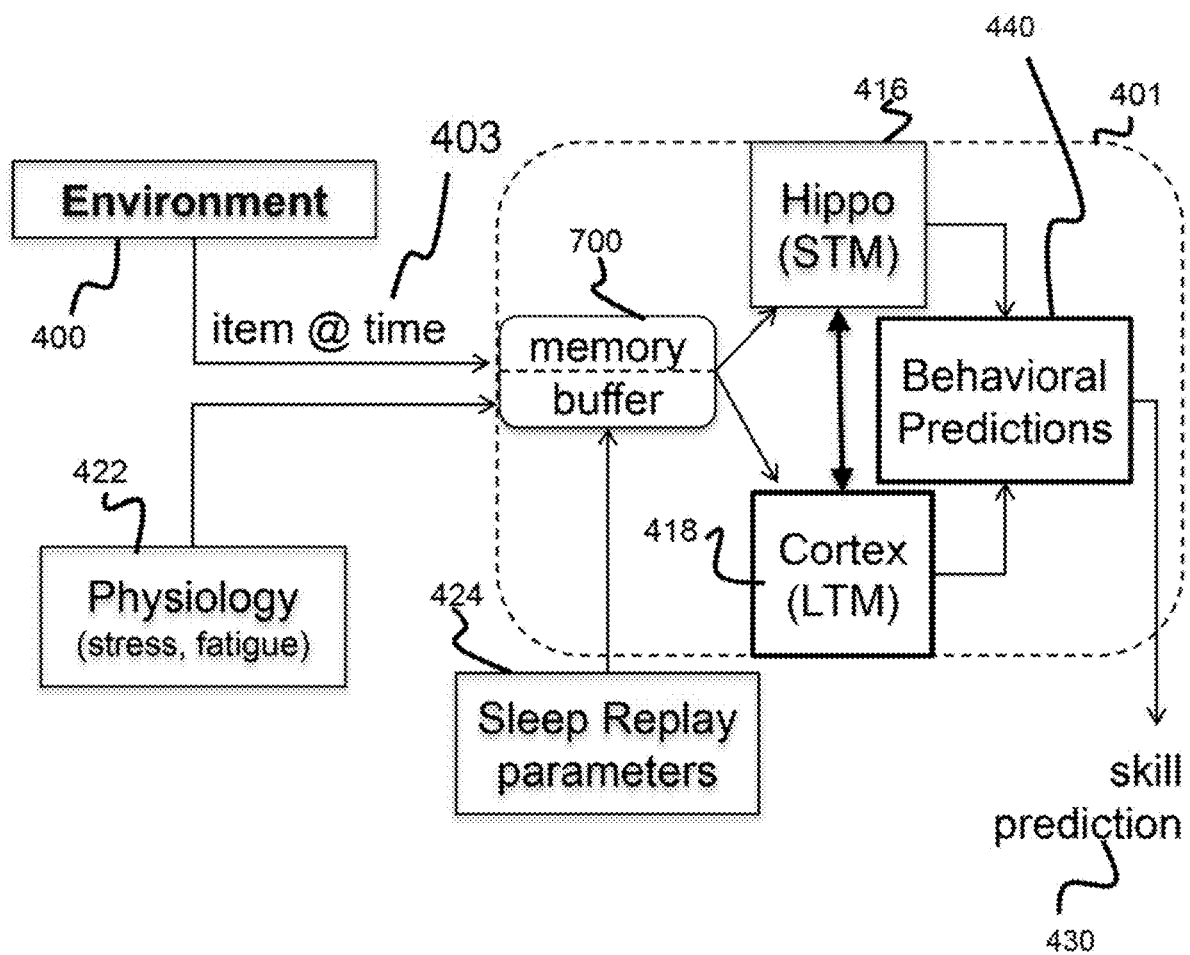
FIG. 4 is an illustration depicting a memory replay model according to various embodiments of the present invention.

The memory replay model 316 or module is illustrated in FIG. 4. This model 316 simulates memory encoding and recall processes in the brain of an individual person ("the subject") during waking and sleeping activities. The square boxes in FIG. 4 represent modular software processes, and the rounded boxes represent buffers through which the modules communicate with each other. The environment box 400 is a special module through which the model 316 interfaces with the environment in which the subject encounters memories of interest.

Vision and Hearing modules can be included as submodules within the environment module 400 that represent the senses of the subject. The Vision and Hearing submodules are responsible to filter the environment and select a single salient item at a time 403. There are, for example, prior art techniques such as visual saliency systems that do a very good job of simulating human vision (See the List of Incorporated Literature References, Reference No. 8), and auditory saliency models simulate human hearing (See the List of Incorporated Literature References, Reference No. 9). For example, if the current goal is to watch for a red truck, the Vision modules will extract any red truck, so it can be symbolized as an item in the memory buffer 700.

As items are represented by frames the memory/buffer 700, they can be registered into the memory 401. FIG. 4 depicts two memory modules, one for short-term memories (STM) 416, one for long-term memories (LTM) 418, and optionally (not depicted) one for procedural memories. Each of these modules 416 and 418 is simulated by a random-access storage data structure holding items in the frame representation described below. Each of these memory modules 416 and 418 has a means of retrieving items that match a search criterion composed of a set of attributes and/or an object type. In the simplest implementation, the single best match in a module is copied into the retrieval buffer of the module. Such a memory system is known to those skilled in the art as a knowledge-based system or an expert system. A desired implementation employs memory and rule execution similar to those in the ACT-R system (see Literature Reference No. 10), which has a memory module like the LTM called "Declarative", and a memory called Procedural that takes the form of a set of rules. The present system also adopts the ACT-R engine that chooses a subset of procedural rules whose constraints are satisfied by items in buffers, and chooses one at a time to "fire". A rule has a set of constraints, and one or more consequents. When the rule is fired, its consequent is executed, and will alter the contents of items in the buffers or in the memories.

The Physiology module 422 represents the effects of stress, fatigue, and attention in the model 316. This affects the activation level of each memory item (described below). A Sleep Replay Parameters module 424 represents the memory consolidation activity experienced by the subject, as sensed by EEG sensors. That will also be described further below in the section on "Personalization, and Behavioral Predictions".

The model 316 can predict (Skill Prediction 430) explicit and implicit memory performance on specific memory related tasks at any time up to a 48-hour period or more following encoding. These predictions are the basis for control of the interventions, ensuring that the specific memory of interest (i.e., first memory, second memory, third memory, etc.) is consolidated just enough, and not too much, to obtain the level of performance required.

(4.2.1) Inputs to the Model

Figure 5:
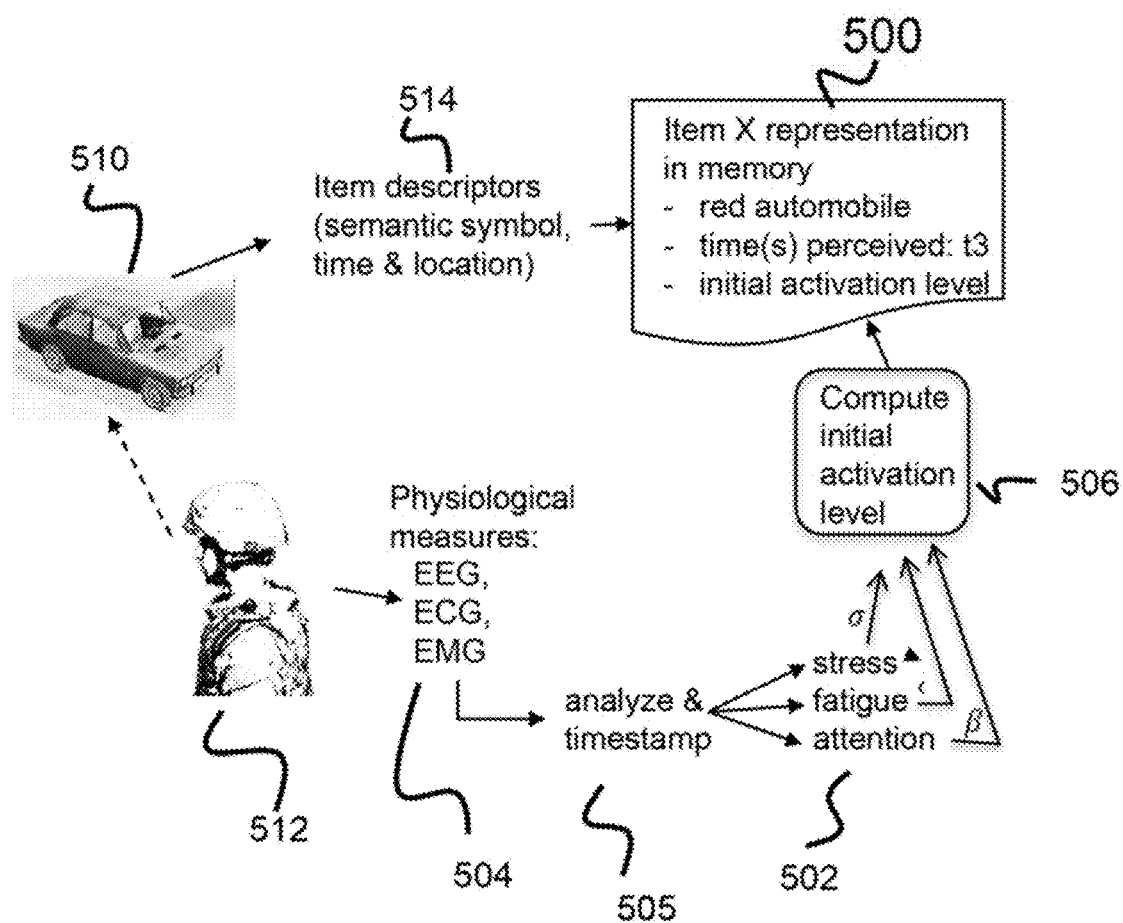
FIG. 5 is an illustration depicting a data structure that represents a memory item ("X") with descriptive attribute pairs and encoding parameters.

The model 316 will simulate the encoding of the specific memories of interest, as well as memories that can conflict with or reinforce those specific memories. As shown in FIG. 5, each memory item is simulated by a frame data structure 500 with a hierarchical type describing the item followed by a set of descriptive attribute-value pairs 514. A data structure 500 represents a memory item ("X") with descriptive attribute-value pairs (e.g., type, color . . . ) 514 and encoding parameters (e.g. timestamp, physiological measures).

The values could be numeric, string, or a reference to another attribute or even another memory item. The hierarchical types are symbolic representations of an ontology of things the user interacts with during the day and may want to remember. The attribute pairs 514 for a particular hierarchical type should be sufficient to describe the salient, discriminative features of the item. The attribute pairs 514 can be provided by the subject or are obtained by using any suitable system that provides item descriptors, such as a semantic symbol, time, and location regarding the item. Any suitable object detection and/or identification system as known to those skilled in the art can be used to obtain such item descriptors.

In addition, each frame data structure 500 includes attributes for time of encoding (when the item was learned or encountered), and physiological measurements 504 taken at the time of encoding (e.g., level of fatigue, stress, alertness). These time-stamped 505 physiological measurements 504 can be measured by standard prior art means using EEG, EMG, and ECG sensor data.

The model 316 is exposed to the same environmental cues (visual, auditory) as those experienced by the subjects 512. Multiple pre-trained deep learning models transform attended multi-modal stimuli (sensed by a video camera and a microphone worn by the subject) into sparse distributed representations (i.e., patterns such as a binary array). Simulating everything seen or heard by a subject during a day would be an intractable problem. There are at least two ways to approach this: (1) As described above, there are saliency algorithms in the prior art capable of selecting the most likely things the subject is attending to. If the subject 512 wears a camera like a GoPro, with a microphone, it can be turned on during times when there is something relevant to be learned. The saliency algorithms identify the most salient items, and they will be represented in the model 316. (2) The subject 512 could be instructed to clearly identify items 510 to be remembered by taking their picture or recording a short phrase. Desirably, the system operates using method 2 where the subject is instructed to identify the items to be remembered.

An "activation level" is computed 506 as a function of attention, fatigue, and stress measurements (denoted by $\beta$, $\delta$, and $\sigma$ in FIG. 5), normalized by measurements taken when the user 512 is well rested, attentive, and at a low level of stress. Thus, a desired implementation for the activation level metric is norm $\{\beta/(\delta*\sigma)\}$, where norm is a normalization function that divides the parameter by the value of that parameter under rested, attentive, low-stress conditions. Since there are indications that some amount of stress actually improves encoding of memories, sigma can be replaced by the amount to which stress differs from such a threshold, so $\sigma$=abs(stress-optimalStress). A desired implementation for optimalStress is 30% of the maximum stress level for the user 512. The activation level 506, so computed, is a dynamic variable of time in the simulation. When a new memory item is registered into memory, it learns relationships with other memories based on their activation levels. The processing of learning relationships is described in further detail below (see Equation 2).

(4.2.2) Operation of the Model

Figure 6:
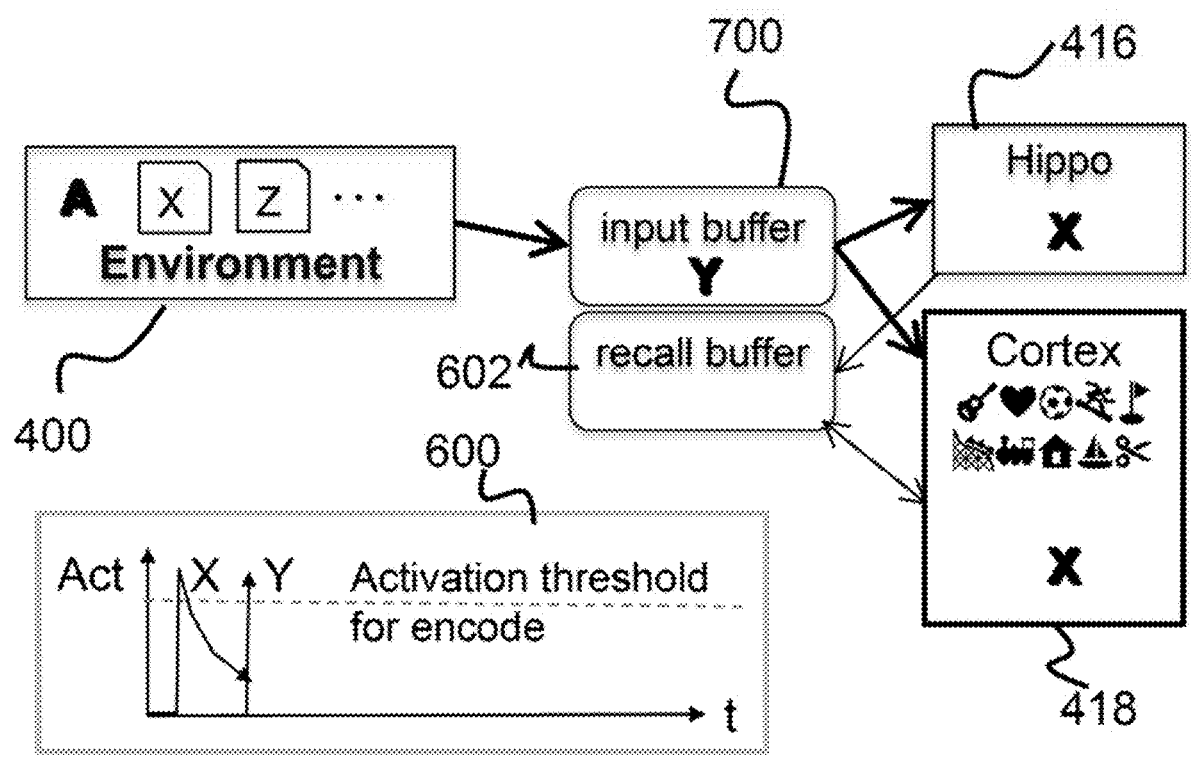
FIG. 6 is an illustration depicting an example operation of the closed-loop model-based control system according to various embodiments of the present invention.

FIG. 6 is an illustration depicting operation of the memory replay model. Items in memory are only as strong as their relationships. The difference between the two memories shown in FIGS. 4 and 6 are that the Hippo (STM) 416 learns relationships quickly and they decay quickly. Cortex (LTM) 418 learns slowly and its memories decay much more slowly. Any perceived item is registered into both memories at once, and learns relationships with other items that are active at the same time, and their own learning rate.

As shown in FIG. 6, as items are encountered in the environment 400, they are given a symbolic representation (a frame) associated with an activation level. In this example, the subject is told to take notice when certain things are seen (here symbolized by the letters Z, X, Y, A, C or B). The Vision sub-module within the Environment module 400 has filtered out an X, which was registered in the Hippo (STM) 416 and Cortex (LTM) 418 modules. The LTM 418 may already be filled with memories from prior experience. The plot 600 represents the activation levels of memory items over time. X activation spikes when X is encountered, and then decays (see Equation 1). When Y is encountered and registered, it forms associations (weighted links (i.e., association strength representations)) with any other items as a function of their activation levels, so X becomes associated with Y, in a directed link.

After item (say, X) is registered in memory (STM 416/LTM 418) and disappears from a recall buffer 602, its activation aX decays as a function of time (t) and connections to other items in memory (wYX):

$$\frac{da_X}{dt} = \delta(t - t_X) - \frac{a_X}{\tau} + \gamma \sum_{Y \neq X} w_{YX} a_Y, \; a_X = \min(a_X, 1). \quad (1)$$

It returns to a high level (baseline modulated by physiology) any time it is registered or practiced ($t_X$). Decay rate ($\tau$) is personalized value, but in general ($\tau_{STM} \gg \tau_{LTM}$). Connections to other items ($w_{YX}$) reduce the decay rate of $a_X$ by an amount gamma ($\gamma$). Gamma is some portion of the learning rate $\eta$, below, and a desired implementation is $\gamma=0.5\eta$. When a new memory item is registered or practiced, associations are formed from any active memory traces (causal connections). For example, if X is in memory with activation $a_X$, and Y is registered with activation $a_Y$, $\eta$ is the learning rate of the memory region ($\eta_{STM} \gg \eta_{LTM}$):

$$\frac{dw_{XY}}{dt} = \eta a_Y \left[ (1 - w_{XY})a_X - w_{XY} \sum_{X^r \neq X} a_{X^r} \right]. \quad (2)$$

(4.3) Memory Cueing and Recall

Figure 7:
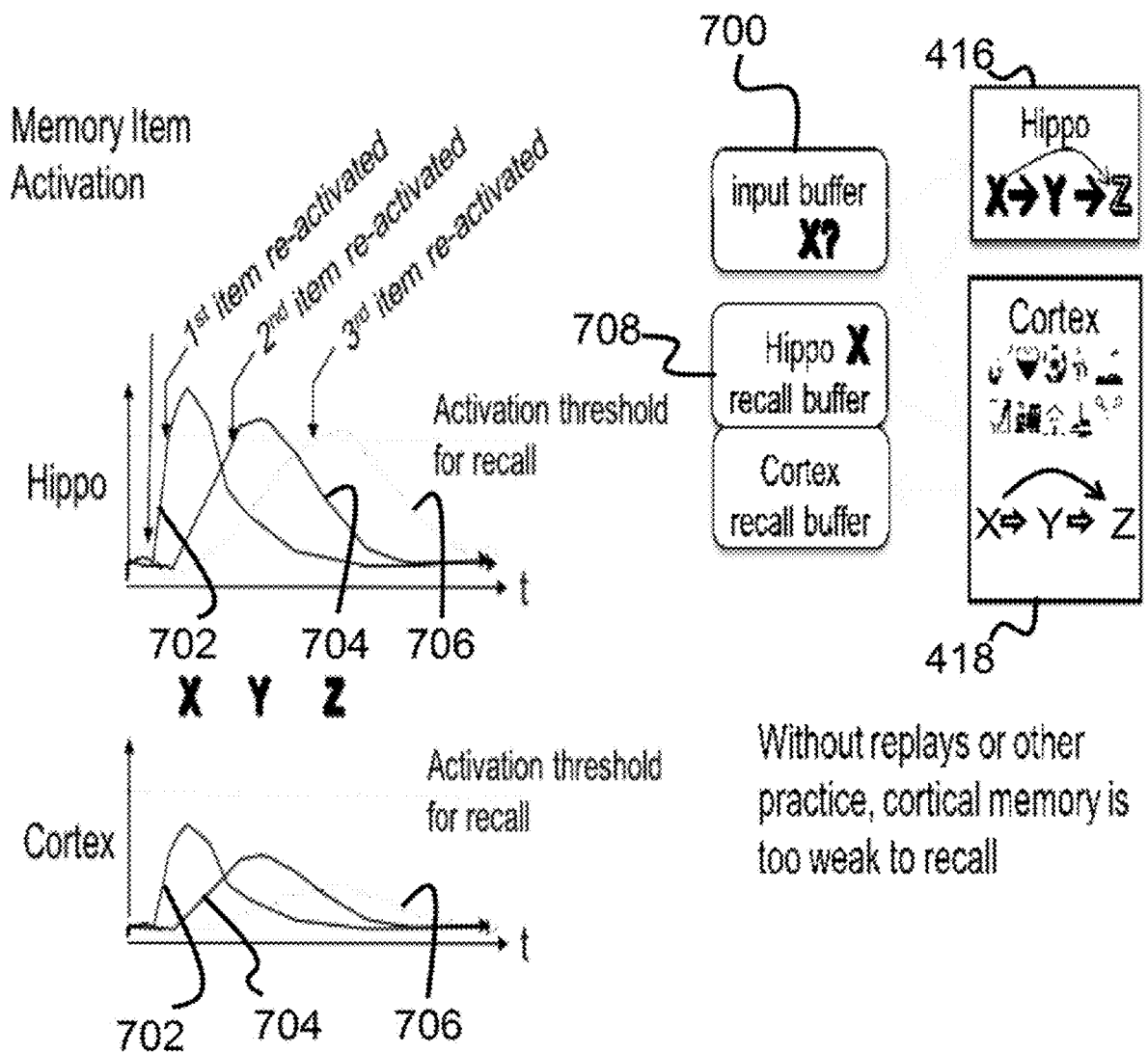
FIG. 7 is an illustration depicting recall of a memory from a short-term memory module.

Once a memory has been stored into the Hippo (STM) 416 and Cortex (LTM) 418, it may be recalled by asserting a cue, or reminder. A cue is part of the memory; it causes the STM 416/LTM 418 to fill in the missing parts. The way an intervention works is that it associates an unrelated percept (e.g., odor, sound, or electrical stimulus) with the memory of interest (i.e., first memory, second memory, third memory, etc.) for use as a cue. Then the memories (i.e., first memory, second memory, third memory, etc.) are induced by presenting that cue. FIG. 7 illustrates how, immediately after learning a reasonably short sequence, in the absence of other confounders or conflicting information it can be recalled from the hippo (STM) 416, but not from the cortex (LTM) 418. This is due to the slow rate of learning in LTM 418. A cue ("X?") is asserted on the input buffer 700, causing a recall cascade of the sequence from STM 416. The activation energy of X 702 in Hippo 416 raises above the recall threshold due to the X? cue, causing it to be recalled from the Hippo 416 (but not from Cortex 418, because cortical memory is very weak after first learning a sequence) and through the Hippo recall buffer 708. Its activation 702 spreads along associations to next item in sequence (the Y activation level 704, which is recalled next, and then spreads to the next (Z item 706).

(4.4) Slow Wave Sleep (SWS) Replay Simulation

Any time a memory is practiced (recalled or replayed) while it is still strong in Hippo (STM), as items are recalled from short term memory, their relationships (i.e., association strength representations) in long-term memory are strengthened. Based on a widely accepted theory backed by experimental data, during sleep memories are "replayed" which is a type of recall from short term memory, but at a higher rate than during waking (6-7 times as fast (see Literature Reference No. 11). This fast replay occurs during slow-wave oscillations (SWOs) in Non-Rapid-Eye-Movement (NREM) sleep, and some have been detected during quiet waking. As FIG. 3 illustrates, the EEG Analyzer 314 will sense the sleep stage and the phase of SWOs. As show in FIG. 8, during the "UP phase" or positive part of the cycle of a SWO, the model raises the activation level of all items in Hippo (STM) by a high noisy energy, just below the threshold 800 for recall. If the activation level of all items in STM have decayed to the same level before the UP phase of SWO, and absent other sources of energy, one of those items can randomly (due to noise) achieve the threshold 800 of activation required for recall (i.e., the model randomly chooses one item in Hippo (STM) and increases its activation level enough to exceed the threshold 800 for replay). When the first item is recalled, its activation spreads on weighted association links, and other items can be recalled in a cascade. Two situations can cause some memories to achieve a higher probability of recall than others, as follows: (1) Due to strength of encoding, recency of encoding, or frequency of practice, some items have a higher activation energy before the SWO UP phase begins, so that when the SWO UP phase adds the high noisy activation to all memories, those memories are much more likely to be replayed. (2) If an intervention is used to cue a specific memory (for example, if an odor or a sound are associated with the memory during waking, and are played again during NREM sleep), the intervention adds energy to that specific memory, likewise raising its probability of being replayed.

Figure 8:
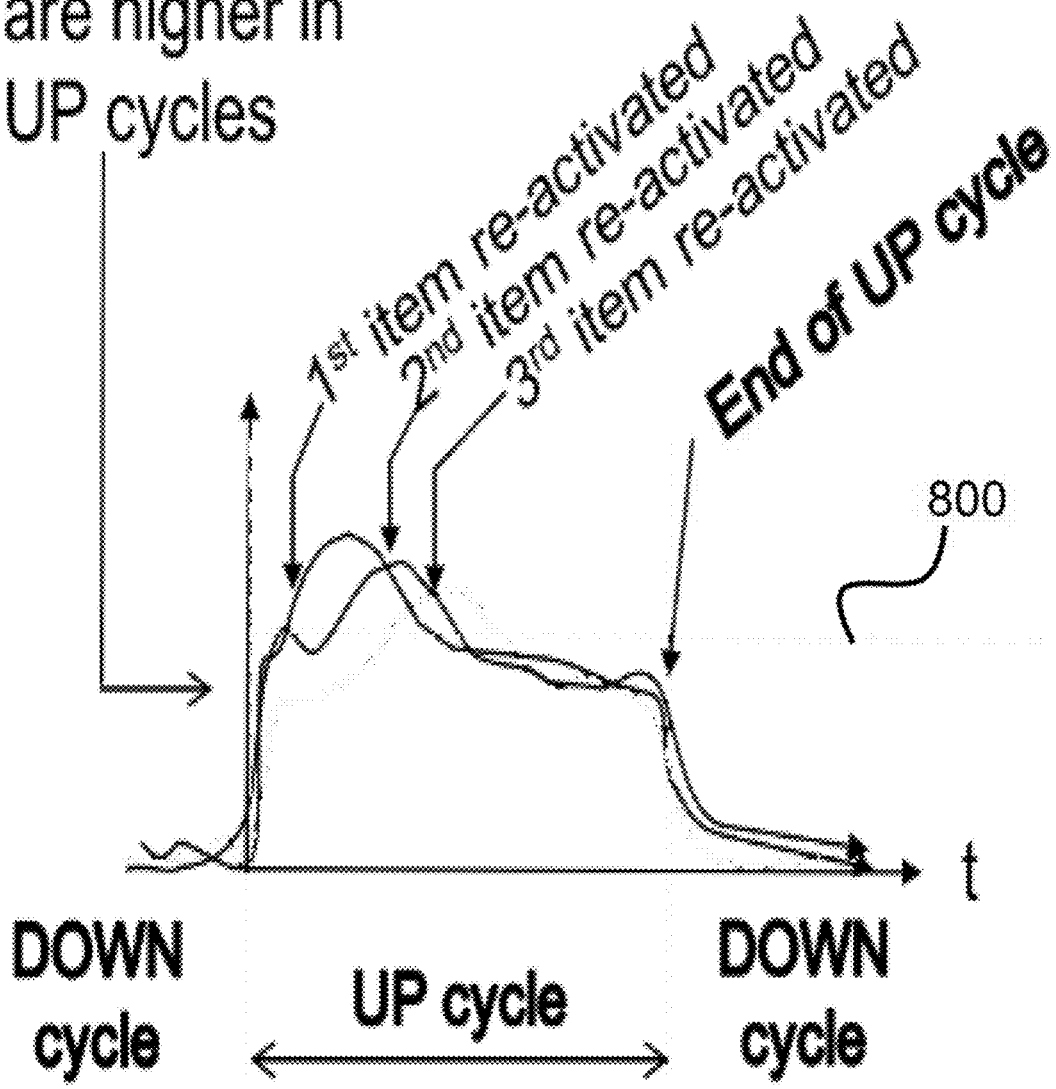
FIG. 8 is an illustration depicting an example of recall cascade.

As mentioned above, when information is recalled from Hippo (STM) during waking, the Cortex (LTM) is exposed to it again, because the output of the STM is one of the inputs to the LTM. This strengthens associations (i.e., association strength representations) of the recalled memory in slower-learning LTM. During sleep replays, since all activation levels are raised, a recall cascade happens much more quickly, so as each item is recalled, the next is already at a high activation. FIG. 8 illustrates a case where the 3 items are recalled faster and each has decayed less when the next is activated. As Equation (2) shows, the association learned between two memories (X and Y) is a function of their activation levels aX and aY. Thus, during a replay the cortex learns a much stronger association than it would have in normal recall.

(4.5) Personalization, and Behavioral Predictions

The memory replay model incorporates measurements of the subject's fatigue, stress, and attention during waking (measured, for example, by prior art techniques). The measurements are delivered as inputs to modulate the initial activation level of the memories when they are learned or trained (the time of memory encoding). Based on memory-relevant physiological states and replay parameters, sensed noninvasively during sleep/wake, the model simulates periods of waking, quiet waking, and the stages of sleep.

Memory consolidation (changes) occurs during slow-wave oscillations in the EEG in the quiet waking and NREM sleep states, so when such states are sensed and reported to the model, the model simulates the strengthening of individual memories. Any suitable sensing technique can be used to report the duration and speed of each SWO, a non-limiting example of such a technique includes that as described in Literature Reference No. 7. Based on the process as described in the previous subsection (SWS Replay Simulation), the model chooses which memory to replay in simulation, strengthening the association weights (i.e., association strength representation) in LTM for that memory.

Each time a replay event occurs, or at regular intervals (e.g., every five, seconds, minutes, etc., or as desired or set by the operator) through the SWS duration, the model will make predictions of behavioral performance (i.e., behavioral prediction 440 as shown in FIG. 4) for the target memory at a given time following acquisition. The behavioral prediction 440 is made by simulating the desired behavior, which is related to the ability to recall the specific memory of interest (i.e., first memory, second memory, third memory, etc.). A cue relevant to the behavior is inserted into the environment module, sensed by the Hearing and Vision submodules based on a particular goal. The behavioral prediction is the recall of the memory item or sequence of items required by the desired behavior. It takes the form of a normalized probability of recall; i.e., how likely is the desired recall compared to other memories in STM and LTM. If predicted performance at a future time of interest is less than a given level, then the model tells the intervention system to apply the target memory cue in the upcoming SWS UP state.

When predicted performance crosses the desired level for that memory, the model ceases intervention for that memory. Other interventions for other memories may continue to operate (e.g., first memory, second memory, third memory, etc.). As a result, the simulation may cause intervention to occur for one or more memories, activating those interventions that are needed to increase memory consolidation (changes) and deactivating those interactions that correspond to memories that are sufficiently consolidated according to their corresponding predicted performance. For example, interventions can be activated for first, second, and third memories, etc. based on corresponding predicted probabilities and/or with interventions that are distinct from each other. This process may continue for some time as a subject is sleeping or is awake and consolidating memories, with individual interventions being turned on and off throughout the period as needed. But replay assessment continues, with incorporation of the parameters of any replay event into the model. Replays of contradictory information acquired in the recent past prior to target encoding, or subsequent to target encoding, could impair future task performance related to the memory of interest (e.g., first memory, second memory, etc.).

For example, in various aspects, an intervention may be turned on, then off, then on again in an evening as the simulation determines that memory consolidation becomes sufficient, weakens too much, and then is strengthened again. At the same time, the simulation may allow other interventions to continue throughout the evening, or may turn them on or off as needed. The memory consolidation may conflict with each other, and the simulation may determine when that conflict necessitates activation of the intervention for a particular memory. In this way, the interventions don't have to be all turned on all the time, resulting in less impact on the subject and more efficient and effective memory consolidation.

Another aspect is tuning the model to match its performance predictions to empirical behavioral data from the user. Model parameters that can be tuned are time constants for learning and weight decay in the neocortex and hippocampus (HC), and modulation parameters for factors such as fatigue, stress, and attention.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A closed-loop control system for memory consolidation in a subject, the system comprising:
   one or more processors and a memory, the memory being a non-transitory computer-readable medium having executable instructions encoded thereon, such that upon execution of the instructions, the one or more processors perform operations of:
   encoding information regarding environmental items as memories in both a long-term memory store and a short-term memory store:
   generating an activation level representation of the first memory, the first memory being a memory of interest related to at least one of the environmental items:
   generating an association strength representation for the memories:
   encoding the first memory in a subject while the subject is coupled to an intervention system and exposed to an environmental item by associating a semantic item description of the environmental item with physiological measurements of the subject;
   predicting behavioral performance for the first memory, the behavioral performance being a probability that the first memory can be recalled on cue; and
   controlling operation of the intervention system with respect to the first memory based on the behavioral performance of the first memory determined by the simulation, wherein controlling operation of the intervention system includes activating at least one intervention selected from a group consisting of transcranial current stimulation, an audio cue, or an odor cue.

2. The closed-loop control system as set forth in claim 1, wherein the encoding information regarding environmental items includes encoding descriptive attribute-value pairs and encoding parameters.

3. The closed-loop control system as set forth in claim 2, wherein simulating memory changes of a first memory in a subject while the subject is coupled to the intervention system is performed when the subject is in non-rapid eye movement (NREM) sleep or waking by strengthening the association strength representation related to the first memory.

4. The closed-loop control system as set forth in claim 3, where information is encoded in both the long-term memory and short-term memory at the same time.

5. The closed-loop control system as set forth in claim 4, wherein an output of the short-term memory is the input of long-term memory, such that when an item is recalled from the short-term memory, the association strength representation for the item are strengthened in the long-term memory.

6. The closed-loop control system as set forth in claim 5, wherein the encoding parameters include both timestamp data and physiological measurements of a subject.

7. The closed-loop control system as set forth in claim 6, wherein the memory of interest is a sequence of events or a single event.

8. The closed-loop control system as set forth in claim 7, wherein the activation level representation is a function of physiological measurements taken at time of encoding the memory of interest.

9. The closed-loop control system as set forth in claim 1, further comprising an operation of tuning at least one of time constants and modulation parameters to cause the predicted behavioral performance match empirical behavioral data of the subject.

10. The closed-loop control system as set forth in claim 1, further comprising an operation of controlling interventions for one or more memories of interest by activating interventions for memories that are needed to increase memory consolidation and deactivating interactions for memories that correspond to memories that are consolidated according to a corresponding predicted performance that exceeds a threshold.

11. A computer program product for closed-loop control for memory consolidation in a subject, the computer program product comprising:
 a non-transitory computer-readable medium having executable instructions encoded thereon, such that upon execution of the instructions by one or more processors, the one or more processors perform operations of:
  encoding information regarding environmental items as memories in both a long-term memory store and a short-term memory store;
  generating an activation level representation of the first memory, the first memory being a memory of interest related to at least one of the environmental items;
  generating an association strength representation for the memories;
  encoding the first memory in a subject while the subject is coupled to an intervention system and exposed to an environmental item by associating a semantic item description of the environmental item with physiological measurements of the subject;
  predicting behavioral performance for the first memory, the behavioral performance being a probability that the first memory can be recalled on cue; and
  controlling operation of the intervention system with respect to the first memory based on the behavioral performance of the first memory determined by the simulation, wherein controlling operation of the intervention system includes activating at least one intervention selected from a group consisting of transcranial current stimulation, an audio cue, or an odor cue.

12. The computer program product as set forth in claim 11, wherein the encoding information regarding environmental items includes encoding descriptive attribute-value pairs and encoding parameters.

13. The computer program product as set forth in claim 12, wherein information is encoded in both the long-term memory and short-term memory at the same time.

14. The computer program product as set forth in claim 13, wherein an output of the short-term memory is the input of long-term memory, such that when an item is recalled from the short-term memory, the association strength representation for the item are strengthened in the long-term memory.

15. The computer program product as set forth in claim 14, wherein the encoding parameters include both timestamp data and physiological measurements of a subject.

16. The computer program product as set forth in claim 15, wherein the memory of interest is a sequence of events or a single event.

17. The computer program product as set forth in claim 16, wherein the activation level representation is a function of physiological measurements taken at time of encoding the memory of interest.

18. A computer implemented method for closed-loop control for memory consolidation in a subject, the method comprising an act of:
 causing one or more processors to execute instructions encoded on a non-transitory computer-readable medium, such that upon execution, the one or more processors perform operations of:
  encoding information regarding environmental items as memories in both a long-term memory store and a short-term memory store;
  generating an activation level representation of the first memory, the first memory being a memory of interest related to at least one of the environmental items;
  generating an association strength representation for the memories;
  encoding the first memory in a subject while the subject is coupled to an intervention system and exposed to an environmental item by associating a semantic item description of the environmental item with physiological measurements of the subject;
  predicting behavioral performance for the first memory, the behavioral performance being a probability that the first memory can be recalled on cue; and
  controlling operation of the intervention system with respect to the first memory based on the behavioral performance of the first memory determined by the simulation, wherein controlling operation of the intervention system includes activating at least one intervention selected from a group consisting of transcranial current stimulation, an audio cue, or an odor cue.

19. The method as set forth in claim 18, wherein the encoding information regarding environmental items includes encoding descriptive attribute-value pairs and encoding parameters.

20. The method as set forth in claim 19, wherein information is encoded in both the long-term memory and short-term memory at the same time.

21. The method as set forth in claim 20, wherein an output of the short-term memory is the input of long-term memory, such that when an item is recalled from the short-term memory, the association strength representation for the item are strengthened in the long-term memory.

22. The method as set forth in claim 21, wherein the encoding parameters include both timestamp data and physiological measurements of a subject.

23. The method as set forth in claim 22, wherein the memory of interest is a sequence of events or a single event.

24. The method as set forth in claim 23, wherein the activation level representation is a function of physiological measurements taken at time of encoding the memory of interest.

* * * * *